(12) United States Patent
Durant et al.

(10) Patent No.: US 11,096,563 B2
(45) Date of Patent: Aug. 24, 2021

(54) METHOD OF DETERMINING THE SHAPE OF A BENDABLE INSTRUMENT

(71) Applicant: INTUITIVE SURGICAL OPERATIONS, INC, Sunnyvale, CA (US)

(72) Inventors: Kevin Durant, Alameda, CA (US); David S. Mintz, Mountain View, CA (US); Robert M. Ohline, Redwood City, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 314 days.

(21) Appl. No.: 15/463,745

(22) Filed: Mar. 20, 2017

(65) Prior Publication Data

US 2017/0251905 A1   Sep. 7, 2017

Related U.S. Application Data

(63) Continuation of application No. 11/603,943, filed on Nov. 21, 2006, now abandoned.
(Continued)

(51) Int. Cl.
*A61B 1/005* (2006.01)
*A61B 34/20* (2016.01)
(Continued)

(52) U.S. Cl.
CPC ........ *A61B 1/0052* (2013.01); *A61B 1/00128* (2013.01); *A61B 5/065* (2013.01);
(Continued)

(58) Field of Classification Search
USPC .......................................... 600/145, 149, 117
See application file for complete search history.

(56) References Cited

U.S. PATENT DOCUMENTS 616,672 A   12/1898 Kelling
2,510,198 A   6/1950 Tesmer
(Continued)

FOREIGN PATENT DOCUMENTS

DE   2823025 A1   12/1979
DE   3707787 A1   9/1988
(Continued)

OTHER PUBLICATIONS

Belson et al., U.S. Appl. No. 11/796,220 entitled "Steerable segmented endoscope and method of insertion" filed Apr. 27, 2007.
(Continued)

*Primary Examiner* — Timothy J Neal
*Assistant Examiner* — Jae Woo
(74) *Attorney, Agent, or Firm* — Haynes and Boone, LLP

(57) ABSTRACT

A method for determining a shape of a bendable instrument can include placing the bendable instrument in a neutral position; moving a first control element a first amount until slack is removed from the first control element; moving a second control element a second amount until slack is removed from the second control element; sensing a position of the first control element after moving the first control element the first amount, the sensed position of the first control element being defined as a first control element calibration position; sensing a position of the second control element after moving the second control element the second amount, the sensed position of the second control element being defined as a second control element calibration position. The method can further include bending the instrument by moving one or both of the first control element and the second control element from the respective first control element calibration position and the second control element calibration position; and determining a resulting shape of the bendable instrument based on a distance one or both of the
(Continued)

first control element and the second control element respectively moved from the first control element calibration position and second control element calibration.

9 Claims, 8 Drawing Sheets

Related U.S. Application Data

(60) Provisional application No. 60/739,353, filed on Nov. 22, 2005.

(51) Int. Cl.
*A61B 5/06* (2006.01)
*A61M 25/01* (2006.01)
*A61B 1/00* (2006.01)
*A61B 90/00* (2016.01)

(52) U.S. Cl.
CPC ......... *A61B 34/20* (2016.02); *A61M 25/0147* (2013.01); *A61M 25/0155* (2013.01); *A61M 25/0158* (2013.01); *A61B 90/361* (2016.02); *A61B 2090/064* (2016.02)

(56) References Cited

U.S. PATENT DOCUMENTS

| | | | |
|---|---|---|---|
| 2,533,494 A | 12/1950 | Mitchell, Jr. | |
| 2,767,705 A | 10/1956 | Moore | |
| 3,060,972 A | 10/1962 | Sheldon | |
| 3,071,161 A | 1/1963 | Ulrich | |
| 3,096,962 A | 7/1963 | Meijs | |
| 3,162,214 A | 12/1964 | Wilfred, Jr. | |
| 3,168,274 A | 2/1965 | Street | |
| 3,190,286 A | 6/1965 | Stokes | |
| 3,266,059 A | 8/1966 | Stelle | |
| 3,430,662 A | 3/1969 | Guarnaschelli | |
| 3,497,083 A | 2/1970 | Victor et al. | |
| 3,546,961 A | 12/1970 | Marton | |
| 3,610,231 A | 10/1971 | Takahashi et al. | |
| 3,625,084 A | 12/1971 | Siebert | |
| 3,643,653 A | 2/1972 | Takahashi et al. | |
| 3,739,770 A | 6/1973 | Mori | |
| 3,773,034 A | 11/1973 | Burns et al. | |
| 3,780,740 A | 12/1973 | Rhea | |
| 3,858,578 A | 1/1975 | Milo | |
| 3,871,358 A | 3/1975 | Fukuda et al. | |
| 3,897,775 A | 8/1975 | Furihata | |
| 3,913,565 A | 10/1975 | Kawahara | |
| 3,946,727 A | 3/1976 | Okada et al. | |
| 3,990,434 A | 11/1976 | Free | |
| 4,054,128 A | 10/1977 | Seufert et al. | |
| 4,176,662 A | 12/1979 | Frazer | |
| 4,233,981 A | 11/1980 | Schomacher | |
| 4,236,509 A | 12/1980 | Takahashi et al. | |
| 4,240,435 A | 12/1980 | Yazawa et al. | |
| 4,273,111 A | 6/1981 | Tsukaya | |
| 4,294,233 A * | 10/1981 | Takahashi | A61B 1/0052 403/43 |
| 4,327,711 A | 5/1982 | Takagi | |
| 4,366,810 A | 1/1983 | Slanetz, Jr. | |
| 4,393,728 A | 7/1983 | Larson et al. | |
| 4,432,349 A | 2/1984 | Oshiro | |
| 4,483,326 A * | 11/1984 | Yamaka | A61B 1/0057 600/141 |
| 4,489,826 A | 12/1984 | Dubson | |
| 4,494,417 A | 1/1985 | Larson et al. | |
| 4,499,895 A | 2/1985 | Takayama | |
| 4,503,842 A | 3/1985 | Takayama | |
| 4,543,090 A | 9/1985 | McCoy | |
| 4,551,061 A | 11/1985 | Olenick | |
| 4,559,928 A * | 12/1985 | Takayama | A61B 1/0052 388/838 |
| 4,566,843 A | 1/1986 | Iwatsuka et al. | |
| 4,577,621 A | 3/1986 | Patel | |
| 4,592,341 A | 6/1986 | Omagari et al. | |
| 4,601,283 A | 7/1986 | Chikama | |
| 4,601,713 A * | 7/1986 | Fuqua | A61M 25/0023 604/103.14 |
| 4,621,618 A | 11/1986 | Omagari | |
| 4,624,243 A | 11/1986 | Lowery et al. | |
| 4,630,649 A | 12/1986 | Oku | |
| 4,643,184 A | 2/1987 | Mobin-Uddin | |
| 4,646,722 A | 3/1987 | Silverstein et al. | |
| 4,648,733 A | 3/1987 | Merkt | |
| 4,651,718 A | 3/1987 | Collins et al. | |
| 4,655,257 A | 4/1987 | Iwashita | |
| 4,683,773 A | 8/1987 | Diamond | |
| 4,686,963 A | 8/1987 | Cohen et al. | |
| 4,688,555 A * | 8/1987 | Wardle | A61B 1/0052 600/149 |
| 4,712,969 A | 12/1987 | Kimura | |
| 4,726,355 A | 2/1988 | Okada | |
| 4,753,222 A | 6/1988 | Morishita | |
| 4,753,223 A | 6/1988 | Bremer | |
| 4,754,909 A | 7/1988 | Barker et al. | |
| 4,784,117 A | 11/1988 | Miyazaki | |
| 4,787,369 A | 11/1988 | Allred, III et al. | |
| 4,788,967 A | 12/1988 | Ueda | |
| 4,793,326 A | 12/1988 | Shishido | |
| 4,796,607 A | 1/1989 | Allred, III et al. | |
| 4,799,474 A | 1/1989 | Ueda | |
| 4,800,890 A | 1/1989 | Cramer | |
| 4,807,593 A | 2/1989 | Ito | |
| 4,815,450 A | 3/1989 | Patel | |
| 4,832,473 A | 5/1989 | Ueda | |
| 4,834,068 A | 5/1989 | Gottesman | |
| 4,873,965 A | 10/1989 | Danieli | |
| 4,873,990 A | 10/1989 | Holmes et al. | |
| 4,879,991 A | 11/1989 | Ogiu | |
| 4,884,557 A | 12/1989 | Takehana et al. | |
| 4,890,602 A | 1/1990 | Hake | |
| 4,895,431 A * | 1/1990 | Tsujiuchi | A61B 1/042 359/29 |
| 4,899,731 A | 2/1990 | Takayama et al. | |
| 4,904,048 A | 2/1990 | Sogawa et al. | |
| 4,917,114 A | 4/1990 | Green et al. | |
| 4,919,112 A * | 4/1990 | Siegmund | A61B 1/00105 600/136 |
| 4,930,494 A | 6/1990 | Takehana et al. | |
| 4,949,927 A | 8/1990 | Madocks et al. | |
| 4,957,486 A | 9/1990 | Davis | |
| 4,969,709 A | 11/1990 | Sogawa et al. | |
| 4,971,035 A | 11/1990 | Ito | |
| 4,977,886 A | 12/1990 | Takehana et al. | |
| 4,977,887 A | 12/1990 | Gouda | |
| 4,982,725 A * | 1/1991 | Hibino | A61B 1/00039 600/104 |
| 4,987,314 A | 1/1991 | Gotanda et al. | |
| 5,005,558 A | 4/1991 | Aomori | |
| 5,005,559 A | 4/1991 | Blanco et al. | |
| 5,014,709 A | 5/1991 | Bjelkhagen et al. | |
| 5,018,509 A | 5/1991 | Suzuki et al. | |
| 5,025,778 A | 6/1991 | Silverstein et al. | |
| 5,060,632 A * | 10/1991 | Hibino | A61B 1/00039 348/65 |
| 5,092,901 A | 3/1992 | Hunter et al. | |
| 5,125,395 A | 6/1992 | Adair | |
| 5,127,393 A | 7/1992 | McFarlin et al. | |
| 5,159,446 A * | 10/1992 | Hibino | A61B 1/00039 348/65 |
| 5,166,787 A * | 11/1992 | Irion | A61B 1/00181 348/75 |
| 5,174,276 A | 12/1992 | Crockard | |
| 5,174,277 A * | 12/1992 | Matsumaru | A61B 1/0055 600/142 |
| 5,188,111 A | 2/1993 | Yates et al. | |
| 5,207,695 A | 5/1993 | Trout, III | |
| 5,217,001 A | 6/1993 | Nakao et al. | |
| 5,220,911 A | 6/1993 | Tamura | |
| 5,228,429 A | 7/1993 | Hatano | |

(56) References Cited

U.S. PATENT DOCUMENTS

| | | | |
|---|---|---|---|
| 5,234,448 A | 8/1993 | Wholey et al. | |
| 5,243,967 A | 9/1993 | Hibino | |
| 5,250,058 A | 10/1993 | Miller et al. | |
| 5,251,611 A | 10/1993 | Zehel et al. | |
| 5,253,647 A | 10/1993 | Takahashi et al. | |
| 5,254,809 A | 10/1993 | Martin | |
| 5,257,617 A | 11/1993 | Takahashi | |
| 5,259,364 A | 11/1993 | Bob et al. | |
| 5,271,381 A | 12/1993 | Ailinger et al. | |
| 5,271,382 A | 12/1993 | Chikama | |
| 5,279,610 A | 1/1994 | Park et al. | |
| 5,297,443 A | 3/1994 | Wentz | |
| 5,299,559 A * | 4/1994 | Bruce | A61B 1/0052 600/141 |
| 5,325,845 A | 7/1994 | Adair | |
| 5,337,732 A | 8/1994 | Grundfest et al. | |
| 5,337,733 A | 8/1994 | Bauerfeind et al. | |
| 5,343,874 A | 9/1994 | Picha et al. | |
| 5,347,987 A | 9/1994 | Feldstein et al. | |
| 5,348,259 A | 9/1994 | Blanco et al. | |
| 5,370,108 A | 12/1994 | Miura et al. | |
| 5,383,467 A | 1/1995 | Auer et al. | |
| 5,383,852 A | 1/1995 | Stevens-Wright | |
| 5,389,222 A | 2/1995 | Shahinpoor | |
| 5,394,864 A | 3/1995 | Kobayashi et al. | |
| 5,400,769 A | 3/1995 | Tanii et al. | |
| 5,402,768 A | 4/1995 | Adair | |
| 5,411,508 A | 5/1995 | Bessler et al. | |
| 5,413,108 A | 5/1995 | Alfano | |
| 5,421,337 A | 6/1995 | Richards-Kortum et al. | |
| 5,425,738 A | 6/1995 | Gustafson et al. | |
| 5,429,118 A | 7/1995 | Cole et al. | |
| 5,439,000 A | 8/1995 | Gunderson et al. | |
| 5,451,221 A * | 9/1995 | Cho | A61B 18/24 606/14 |
| 5,456,714 A | 10/1995 | Owen | |
| 5,460,166 A | 10/1995 | Yabe et al. | |
| 5,460,168 A | 10/1995 | Masubuchi et al. | |
| 5,469,840 A * | 11/1995 | Tanii | A61B 1/00039 600/109 |
| 5,482,029 A | 1/1996 | Sekiguchi et al. | |
| 5,487,757 A | 1/1996 | Truckai et al. | |
| 5,489,256 A * | 2/1996 | Adair | A61B 1/00073 600/123 |
| 5,507,287 A | 4/1996 | Palcic et al. | |
| 5,507,717 A | 4/1996 | Kura et al. | |
| 5,531,664 A | 7/1996 | Adachi et al. | |
| 5,551,945 A * | 9/1996 | Yabe | A61B 1/00142 600/121 |
| 5,558,619 A | 9/1996 | Kami et al. | |
| 5,558,665 A | 9/1996 | Kieturakis | |
| 5,577,992 A | 11/1996 | Chiba et al. | |
| 5,586,968 A | 12/1996 | Grundl et al. | |
| 5,590,660 A | 1/1997 | MacAulay et al. | |
| 5,601,087 A | 2/1997 | Gunderson et al. | |
| 5,602,449 A | 2/1997 | Krause et al. | |
| 5,620,408 A | 4/1997 | Vennes et al. | |
| 5,624,380 A | 4/1997 | Takayama et al. | |
| 5,624,381 A | 4/1997 | Kieturakis | |
| 5,626,553 A | 5/1997 | Frassica et al. | |
| 5,645,520 A | 7/1997 | Nakamura et al. | |
| 5,647,368 A | 7/1997 | Zeng et al. | |
| 5,651,769 A | 7/1997 | Waxman et al. | |
| 5,653,690 A * | 8/1997 | Booth | A61M 25/04 604/103.07 |
| 5,658,238 A | 8/1997 | Suzuki et al. | |
| 5,662,585 A * | 9/1997 | Willis | A61B 1/00087 600/104 |
| 5,662,587 A | 9/1997 | Grundfest et al. | |
| 5,665,050 A | 9/1997 | Benecke | |
| 5,667,476 A | 9/1997 | Frassica et al. | |
| 5,679,216 A | 10/1997 | Takayama et al. | |
| 5,728,044 A | 3/1998 | Shan | |
| 5,733,245 A | 3/1998 | Kawano | |
| 5,749,828 A | 5/1998 | Solomon et al. | |
| 5,752,912 A | 5/1998 | Takahashi et al. | |
| 5,759,151 A | 6/1998 | Sturges | |
| 5,762,613 A | 6/1998 | Sutton et al. | |
| 5,765,561 A * | 6/1998 | Chen | G09B 23/28 348/77 |
| 5,769,792 A | 6/1998 | Palcic et al. | |
| 5,772,597 A | 6/1998 | Goldberger et al. | |
| 5,773,835 A | 6/1998 | Sinofsky | |
| 5,779,624 A | 7/1998 | Chang | |
| 5,807,241 A | 9/1998 | Heimberger | |
| 5,810,715 A | 9/1998 | Moriyama | |
| 5,810,716 A | 9/1998 | Mukherjee et al. | |
| 5,810,717 A | 9/1998 | Maeda et al. | |
| 5,810,776 A * | 9/1998 | Bacich | A61B 17/3417 604/131 |
| 5,813,976 A | 9/1998 | Filipi et al. | |
| 5,827,190 A | 10/1998 | Palcic et al. | |
| 5,842,973 A | 12/1998 | Bullard | |
| 5,860,581 A | 1/1999 | Robertson et al. | |
| 5,860,914 A | 1/1999 | Chiba et al. | |
| 5,876,329 A | 3/1999 | Harhen | |
| 5,876,373 A | 3/1999 | Giba et al. | |
| 5,885,208 A | 3/1999 | Moriyama | |
| 5,893,369 A * | 4/1999 | LeMole | A61B 17/11 606/184 |
| 5,897,417 A | 4/1999 | Grey | |
| 5,897,488 A | 4/1999 | Ueda | |
| 5,902,254 A | 5/1999 | Magram | |
| 5,906,591 A | 5/1999 | Dario et al. | |
| 5,908,381 A | 6/1999 | Aznoian et al. | |
| 5,912,147 A | 6/1999 | Stoler et al. | |
| 5,916,147 A | 6/1999 | Boury | |
| 5,921,915 A | 7/1999 | Aznoian et al. | |
| 5,928,136 A | 7/1999 | Barry | |
| 5,941,815 A | 8/1999 | Chang | |
| 5,941,908 A | 8/1999 | Goldsteen et al. | |
| 5,944,690 A * | 8/1999 | Falwell | A61M 25/0147 600/146 |
| 5,957,833 A | 9/1999 | Shan | |
| 5,968,052 A * | 10/1999 | Sullivan, III | A61F 2/95 606/206 |
| 5,971,767 A | 10/1999 | Kaufman et al. | |
| 5,976,074 A | 11/1999 | Moriyama | |
| 5,989,182 A | 11/1999 | Hori et al. | |
| 5,989,230 A | 11/1999 | Frassica | |
| 5,993,381 A | 11/1999 | Ito | |
| 5,993,447 A * | 11/1999 | Blewett | A61B 18/1477 600/105 |
| 5,996,346 A | 12/1999 | Maynard | |
| 6,016,440 A | 1/2000 | Simon et al. | |
| 6,033,359 A | 3/2000 | Doi | |
| 6,036,636 A | 3/2000 | Motoki et al. | |
| 6,042,155 A | 3/2000 | Lockwood | |
| 6,048,307 A | 4/2000 | Grundl et al. | |
| 6,063,022 A * | 5/2000 | Ben-Haim | A61B 34/20 600/41 |
| 6,066,102 A | 5/2000 | Townsend et al. | |
| 6,066,132 A | 5/2000 | Chen et al. | |
| 6,068,638 A * | 5/2000 | Makower | A61B 1/3137 606/159 |
| 6,096,289 A | 8/2000 | Goldenberg | |
| 6,099,464 A | 8/2000 | Shimizu et al. | |
| 6,099,465 A * | 8/2000 | Inoue | A61B 1/05 348/75 |
| 6,099,485 A | 8/2000 | Patterson | |
| 6,106,510 A | 8/2000 | Lunn et al. | |
| 6,119,913 A | 9/2000 | Adams et al. | |
| 6,129,667 A | 10/2000 | Dumoulin et al. | |
| 6,129,683 A | 10/2000 | Sutton et al. | |
| 6,141,577 A | 10/2000 | Rolland et al. | |
| 6,149,581 A | 11/2000 | Klingenstein | |
| 6,162,171 A | 12/2000 | Ng et al. | |
| 6,174,280 B1 | 1/2001 | Oneda et al. | |
| 6,174,291 B1 | 1/2001 | McMahon et al. | |
| 6,179,776 B1 | 1/2001 | Adams et al. | |
| 6,185,448 B1 * | 2/2001 | Borovsky | A61B 5/06 600/424 |

(56) References Cited

U.S. PATENT DOCUMENTS

| | | | |
|---|---|---|---|
| 6,201,989 B1 | 3/2001 | Whitehead et al. | |
| 6,203,493 B1 | 3/2001 | Ben-Haim | |
| 6,203,494 B1 | 3/2001 | Moriyama | |
| 6,210,337 B1 | 4/2001 | Dunham et al. | |
| 6,221,006 B1 | 4/2001 | Dubrul et al. | |
| 6,241,657 B1 | 6/2001 | Chen et al. | |
| 6,249,076 B1 | 6/2001 | Madden et al. | |
| 6,270,453 B1 | 8/2001 | Sakai | |
| 6,272,371 B1* | 8/2001 | Shlomo | A61B 34/20 |
| | | | 128/899 |
| 6,306,081 B1 | 10/2001 | Ishikawa et al. | |
| 6,309,346 B1 | 10/2001 | Farhadi | |
| 6,315,714 B1 | 11/2001 | Akiba | |
| 6,319,197 B1* | 11/2001 | Tsuji | H04N 7/183 |
| | | | 348/E7.087 |
| 6,327,492 B1 | 12/2001 | Lemelson | |
| 6,332,089 B1 | 12/2001 | Acker et al. | |
| 6,348,058 B1 | 2/2002 | Melkent et al. | |
| 6,366,799 B1 | 4/2002 | Acker et al. | |
| 6,402,687 B1 | 6/2002 | Ouchi | |
| 6,408,889 B1 | 6/2002 | Komachi | |
| 6,428,203 B1 | 8/2002 | Danley | |
| 6,443,888 B1* | 9/2002 | Ogura | A61B 1/00124 |
| | | | 600/132 |
| 6,453,190 B1 | 9/2002 | Acker et al. | |
| 6,459,481 B1 | 10/2002 | Schaack | |
| 6,468,203 B2 | 10/2002 | Belson | |
| 6,482,149 B1 | 11/2002 | Torii | |
| 6,485,413 B1 | 11/2002 | Boppart et al. | |
| 6,490,467 B1 | 12/2002 | Bucholz et al. | |
| 6,511,417 B1 | 1/2003 | Taniguchi et al. | |
| 6,511,418 B2 | 1/2003 | Shahidi et al. | |
| 6,517,477 B1 | 2/2003 | Wendlandt | |
| 6,527,706 B2 | 3/2003 | Ide | |
| 6,537,211 B1 | 3/2003 | Wang et al. | |
| 6,544,215 B1 | 4/2003 | Bencini et al. | |
| 6,554,793 B1 | 4/2003 | Pauker et al. | |
| 6,569,173 B1 | 5/2003 | Blatter et al. | |
| 6,616,600 B2 | 9/2003 | Pauker | |
| 6,638,213 B2 | 10/2003 | Ogura et al. | |
| 6,641,528 B2 | 11/2003 | Torii | |
| 6,656,110 B1 | 12/2003 | Irion et al. | |
| 6,699,183 B1 | 3/2004 | Wimmer | |
| 6,761,685 B2 | 7/2004 | Adams et al. | |
| 6,783,491 B2 | 8/2004 | Saadat et al. | |
| 6,790,173 B2 | 9/2004 | Saadat et al. | |
| 6,800,056 B2 | 10/2004 | Tartaglia et al. | |
| 6,808,499 B1* | 10/2004 | Churchill | A61H 39/002 |
| | | | 600/587 |
| 6,808,520 B1* | 10/2004 | Fourkas | A61B 17/3462 |
| | | | 604/164.09 |
| 6,817,973 B2 | 11/2004 | Merril et al. | |
| 6,837,846 B2 | 1/2005 | Jaffe et al. | |
| 6,837,847 B2 | 1/2005 | Ewers et al. | |
| 6,837,849 B2 | 1/2005 | Ogura et al. | |
| 6,843,793 B2 | 1/2005 | Brock et al. | |
| 6,850,794 B2 | 2/2005 | Shahidi | |
| 6,858,005 B2 | 2/2005 | Ohline et al. | |
| 6,869,396 B2 | 3/2005 | Belson | |
| 6,875,170 B2 | 4/2005 | Francois et al. | |
| 6,890,297 B2 | 5/2005 | Belson | |
| 6,902,528 B1 | 6/2005 | Garibaldi et al. | |
| 6,942,613 B2 | 9/2005 | Ewers et al. | |
| 6,960,161 B2* | 11/2005 | Amling | A61B 1/00119 |
| | | | 600/110 |
| 6,960,162 B2 | 11/2005 | Saadat et al. | |
| 6,960,163 B2 | 11/2005 | Ewers et al. | |
| 6,974,411 B2 | 12/2005 | Belson | |
| 6,984,203 B2 | 1/2006 | Tartaglia et al. | |
| 7,018,331 B2* | 3/2006 | Chang | A61B 1/00059 |
| | | | 385/101 |
| 7,060,027 B2* | 6/2006 | Maeda | A61B 1/00039 |
| | | | 600/117 |
| 7,087,013 B2* | 8/2006 | Belson | A61B 1/0053 |
| | | | 600/145 |
| 2002/0016607 A1* | 2/2002 | Bonadio | A61B 17/3423 |
| | | | 606/192 |
| 2002/0062062 A1 | 5/2002 | Belson et al. | |
| 2002/0120254 A1 | 8/2002 | Julian et al. | |
| 2002/0147385 A1 | 10/2002 | Butler et al. | |
| 2002/0151767 A1 | 10/2002 | Sonnenschein et al. | |
| 2002/0169361 A1 | 11/2002 | Taniguchi et al. | |
| 2002/0193662 A1 | 12/2002 | Belson | |
| 2003/0045778 A1* | 3/2003 | Ohline | A61B 1/0053 |
| | | | 600/114 |
| 2003/0083550 A1 | 5/2003 | Miyagi | |
| 2003/0130598 A1 | 7/2003 | Manning et al. | |
| 2003/0167007 A1 | 9/2003 | Belson | |
| 2003/0182091 A1* | 9/2003 | Kukuk | G05B 17/02 |
| | | | 703/2 |
| 2003/0195387 A1 | 10/2003 | Kortenbach et al. | |
| 2003/0233056 A1 | 12/2003 | Saadat et al. | |
| 2003/0236505 A1 | 12/2003 | Bonadio et al. | |
| 2003/0236549 A1 | 12/2003 | Bonadio et al. | |
| 2004/0019254 A1 | 1/2004 | Belson et al. | |
| 2004/0034279 A1* | 2/2004 | Arai | A61B 1/00039 |
| | | | 600/152 |
| 2004/0044270 A1 | 3/2004 | Barry | |
| 2004/0049251 A1 | 3/2004 | Knowlton | |
| 2004/0097788 A1 | 5/2004 | Mourlas et al. | |
| 2004/0106852 A1 | 6/2004 | Windheuser et al. | |
| 2004/0138530 A1* | 7/2004 | Kawai | A61B 1/0051 |
| | | | 600/152 |
| 2004/0167553 A1* | 8/2004 | Simpson | A61B 17/320758 |
| | | | 606/159 |
| 2004/0176683 A1 | 9/2004 | Whitin et al. | |
| 2004/0186350 A1 | 9/2004 | Brenneman et al. | |
| 2004/0193008 A1 | 9/2004 | Jaffe et al. | |
| 2004/0193009 A1 | 9/2004 | Jaffe et al. | |
| 2004/0210109 A1 | 10/2004 | Jaffe et al. | |
| 2004/0220450 A1 | 11/2004 | Jaffe et al. | |
| 2004/0230096 A1* | 11/2004 | Stefanchik | A61B 1/00073 |
| | | | 600/106 |
| 2005/0020901 A1 | 1/2005 | Belson et al. | |
| 2005/0085693 A1 | 4/2005 | Belson et al. | |
| 2005/0119527 A1* | 6/2005 | Banik | A61B 1/00059 |
| | | | 600/117 |
| 2005/0124855 A1 | 6/2005 | Jaffe et al. | |
| 2005/0137454 A1 | 6/2005 | Saadat et al. | |
| 2005/0137455 A1 | 6/2005 | Ewers et al. | |
| 2005/0137456 A1 | 6/2005 | Saadat et al. | |
| 2005/0154258 A1 | 7/2005 | Tartaglia et al. | |
| 2005/0154261 A1 | 7/2005 | Ohline et al. | |
| 2005/0165276 A1 | 7/2005 | Belson et al. | |
| 2005/0168571 A1* | 8/2005 | Lia | A61B 1/05 |
| | | | 348/82 |
| 2005/0203339 A1 | 9/2005 | Butler et al. | |
| 2005/0209506 A1 | 9/2005 | Butler et al. | |
| 2005/0209509 A1 | 9/2005 | Belson | |
| 2005/0222497 A1 | 10/2005 | Belson | |
| 2005/0222498 A1 | 10/2005 | Belson | |
| 2005/0250990 A1 | 11/2005 | Le et al. | |
| 2006/0009678 A1 | 1/2006 | Jaffe et al. | |
| 2006/0015012 A1* | 1/2006 | Sato | A61B 1/00006 |
| | | | 600/118 |
| 2006/0052664 A1 | 3/2006 | Julian et al. | |
| 2006/0111612 A1* | 5/2006 | Matsumoto | A61B 1/00089 |
| | | | 600/129 |
| 2006/0235457 A1 | 10/2006 | Belson | |
| 2006/0235458 A1 | 10/2006 | Belson | |
| 2006/0258912 A1 | 11/2006 | Belson et al. | |
| 2007/0043259 A1 | 2/2007 | Jaffe et al. | |
| 2007/0093858 A1 | 4/2007 | Gambale et al. | |
| 2007/0112255 A1* | 5/2007 | Ikeda | A61B 1/00039 |
| | | | 600/146 |
| 2007/0135803 A1 | 6/2007 | Belson | |
| 2007/0161291 A1 | 7/2007 | Swinehart et al. | |
| 2007/0173694 A1* | 7/2007 | Tsuji | A61B 1/0005 |
| | | | 600/146 |
| 2007/0249901 A1 | 10/2007 | Ohline et al. | |
| 2007/0270650 A1 | 11/2007 | Eno et al. | |

(56) References Cited

U.S. PATENT DOCUMENTS

| | | | |
|---|---|---|---|
| 2008/0154288 A1* | 6/2008 | Belson | A61B 1/00147 606/150 |
| 2010/0210908 A1* | 8/2010 | Ashida | A61B 1/0052 600/145 |
| 2012/0046522 A1* | 2/2012 | Naito | A61B 1/00006 600/118 |
| 2014/0222214 A1* | 8/2014 | Tojo | G02B 23/2476 700/275 |

FOREIGN PATENT DOCUMENTS

| | | |
|---|---|---|
| DE | 4102211 A1 | 8/1991 |
| DE | 19626433 A1 | 1/1998 |
| DE | 19729499 A1 | 1/1999 |
| EP | 0165718 A2 | 12/1985 |
| EP | 382974 A1 | 8/1990 |
| EP | 497781 A1 | 8/1992 |
| EP | 0993804 A1 | 4/2000 |
| EP | 1101442 A2 | 5/2001 |
| EP | 1681013 A1 | 7/2006 |
| FR | 2732225 A1 | 10/1996 |
| GB | 2347685 A | 9/2000 |
| IE | 20000559 | 7/2000 |
| IE | 20020170 | 3/2002 |
| JP | 63136014 A2 | 6/1988 |
| JP | 63272322 A2 | 11/1988 |
| JP | 1152413 A2 | 6/1989 |
| JP | 1229220 A2 | 9/1989 |
| JP | 1262372 A2 | 10/1989 |
| JP | 2246986 A2 | 10/1990 |
| JP | 2296209 A2 | 12/1990 |
| JP | 3136630 A2 | 6/1991 |
| JP | 4054970 A2 | 2/1992 |
| JP | 5011196 A2 | 1/1993 |
| JP | 5111458 A2 | 5/1993 |
| JP | 5305073 A2 | 11/1993 |
| JP | 6007287 A2 | 1/1994 |
| JP | 8322786 A2 | 12/1996 |
| JP | 9028662 A2 | 2/1997 |
| JP | 10337274 A2 | 12/1998 |
| JP | 11042258 A2 | 2/1999 |
| JP | 2000300511 A | 10/2000 |
| JP | 21046318 A2 | 2/2001 |
| SU | 871786 A1 | 10/1981 |
| SU | 1256955 A1 | 9/1986 |
| SU | 1301701 A1 | 4/1987 |
| WO | WO-199317751 A1 | 9/1993 |
| WO | WO-199419051 A1 | 9/1994 |
| WO | WO-199504556 A2 | 2/1995 |
| WO | WO-9509562 A1 | 4/1995 |
| WO | WO-9605768 A1 | 2/1996 |
| WO | WO-199710746 A1 | 3/1997 |
| WO | WO-9725101 A2 | 7/1997 |
| WO | WO-9729701 A1 | 8/1997 |
| WO | WO-9729710 A1 | 8/1997 |
| WO | WO-199824017 A2 | 6/1998 |
| WO | WO-9849938 A1 | 11/1998 |
| WO | WO-199916359 A1 | 4/1999 |
| WO | WO-199933392 A1 | 7/1999 |
| WO | WO-199951283 A2 | 10/1999 |
| WO | WO-199959664 A1 | 11/1999 |
| WO | WO-0010456 A1 | 3/2000 |
| WO | WO-200010466 A1 | 3/2000 |
| WO | WO-200027462 A1 | 5/2000 |
| WO | WO-200054653 A1 | 9/2000 |
| WO | WO-200074565 A1 | 12/2000 |
| WO | WO-200149353 A2 | 7/2001 |
| WO | WO-200167964 A2 | 9/2001 |
| WO | WO-200170096 A1 | 9/2001 |
| WO | WO-200170097 A1 | 9/2001 |
| WO | WO-0174235 A1 | 10/2001 |
| WO | WO-200180935 A1 | 11/2001 |
| WO | WO-200224058 A2 | 3/2002 |
| WO | WO-200239909 A1 | 5/2002 |
| WO | WO-200247549 A1 | 6/2002 |
| WO | WO-200264028 A1 | 8/2002 |
| WO | WO-200268988 A1 | 9/2002 |
| WO | WO-200269841 A2 | 9/2002 |
| WO | WO-200289692 A1 | 11/2002 |
| WO | WO-200296276 A1 | 12/2002 |
| WO | WO-03028547 A2 | 4/2003 |
| WO | WO-03073920 A2 | 9/2003 |
| WO | WO-200373921 A1 | 9/2003 |
| WO | WO-03092476 A2 | 11/2003 |
| WO | WO-200406980 A2 | 1/2004 |
| WO | WO-2004019769 A1 | 3/2004 |
| WO | WO-2004049905 A2 | 6/2004 |
| WO | WO-200471284 A1 | 8/2004 |
| WO | WO-200480313 A1 | 9/2004 |
| WO | WO-2004084702 A2 | 10/2004 |
| WO | WO-200584542 A1 | 9/2005 |
| WO | WO-2006134881 A1 | 12/2006 |

OTHER PUBLICATIONS

Berger, W. L. et al., "Sigmoid Stiffener for Decompression Tube Placement in Colonic Pseudo-Obstruction," Endoscopy, 2000, vol. 32, Issue 1, pp. 54-57.

Durant, et al.; U.S. Appl. No. 12/036,976 entitled "Systems and methods for articulating an elongate body," filed Feb. 25, 2008.

Extended European Search Report for Application No. 20060838329, dated Dec. 18, 2009, 7 pages.

Hasson, H.M., "Technique of Open Laparoscopy," (from step 1 to step 9), May 1979, 2424 North Clark Street, Chicago, Illinois 60614, 3 pages.

International Search Report and Written Opinion for Application No. PCT/US2006/045304, dated Jun. 18, 2008, 4 pages.

Laptop Magazine, Science & Technology section, Oct. 2002, pp. 98, 100, and 102.

Lee, Thomas S. et al., "A highly redundant robot system for inspection," Proceedings of Conference on Intelligent Robotics in Field, Factory, Service, and Space (CIRFFSS '94). Mar. 21-24, 1994. vol. 1, pp. 142-148. Houston, Texas.

Mckernan, J.B. et al., "Laparoscopic general surgery," Journal of the Medical Association of Georgia, Mar. 1990, vol. 79, Issue 3, pp. 157-159.

Slatkin, A.B. et al., "The development of a robotic endoscope," Proceedings 1995 IEEE/RSJ International Conference on Intelligent Robots and Systems, Aug. 5-9, 1995, vol. 2, pp. 162-171, Pittsburgh, Pennsylvania.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Woodley et al., U.S. Appl. No. 11/871,104 entitled "System for managing bowden cables in articulating instruments," filed Oct. 11, 2007.

Extended European Search Report for Application No. EP20189123.1 dated Feb. 4, 2021, 07 pages.

Ireland Application No. 2000/0225 filed on Mar. 22, 2000, Inventor Declan B., et al.

\* cited by examiner

METHOD OF DETERMINING THE SHAPE OF A BENDABLE INSTRUMENT

CROSS-REFERENCE TO RELATED APPLICATIONS

This application is a continuation application of U.S. patent application Ser. No. 11/603,943, filed on Nov. 21, 2006, which claims the benefit of priority to U.S. Provisional Patent Application No. 60/739,353 entitled "Method For Measuring Angle of Articulating Segment Using Complementary Control Wires" filed Nov. 22, 2005, each of which is incorporated herein by reference in its entirety.

BACKGROUND OF THE INVENTION

Bendable instruments come in many forms such as catheters, colonoscopes, endoscopes and the like. Control elements are used to bend the instruments into a desired shape or as part of steering or maneuvering the instrument as needed for a surgical or exploratory procedure for example. While the instrument may be controlled to ultimately reach a desired position, knowing the shape of the instrument may provide useful information for maneuvering the instrument or to aid in the procedure.

What are needed are improved techniques for identifying the shape of a bendable instrument.

SUMMARY OF THE INVENTION

One embodiment of the invention provides method of determining the shape of a bendable instrument by moving at least two control elements first and second amounts without bending the instrument; measuring the first and second amounts; and determining the shape of the instrument from the first and second amounts. In one alternative, the moving step is accomplished without using an actuator connected to a control element. In another alternative, the moving step removes slack from the at least two control elements before the measuring step. In one aspect, the removing step is performed by applying a known drive command to an actuator. In one embodiment, the drive command is insufficient to change the position of the instrument. In one embodiment, the drive command is the current applied to an actuator. In another embodiment, the removing step is performed using a tension measurement taken in a connector that couples an actuator to one of the at least two control elements. In another embodiment, the removing step is performed using a feedback loop that receives input from a sensor. In one aspect, the input from a sensor is related to a tension measurement of a control element. In one embodiment, the sensor is located on or in the bendable instrument. In another embodiment, the sensor is located on or in a connector that joins the bendable instrument to an actuator. In yet another aspect, the sensor is located on or in an actuator connected to a control element.

In another alternative, a step is performed by removing the slack from the at least two control elements during a first time period at a first force limit before removing the slack from the at least two control elements during a second time period at a second different force limit. In one aspect, the first force limit is less than the second force limit.

In another embodiment, the determining step uses a look up table that correlates the first and second amounts to the instrument shape, position or configuration. In another aspect, the determining step uses a modeled kinematic relationship between first and second amounts and the instrument shape, position or configuration. In another aspect, the determining step uses a calculated position delta of the at least two control elements. In another aspect, the determining step uses a calculated position delta of complementary control elements within the at least two control elements. In another aspect, the determining step uses a calculated position delta of a pair of opposing control elements within the at least two control elements. In yet another alternative embodiment, the measuring step includes the steps of (a) moving a control element not being used to bend the instrument; and (b) determining a calculated position delta for the control element not being used to bend the instrument. In one aspect, the determining step uses the calculated position delta for a control element not being used to bend the instrument.

In one alternative, the step of positioning the bendable instrument within a lumen is performed before the moving step. In another aspect, the moving step is performed by the lumen acting on the instrument. In another aspect, the determining step is used to determine the shape of the lumen.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

There are a number of articulating instruments, bendable instruments and steerable instruments available. Examples of such instruments and various control systems are described in, for example, U.S. Pat. Nos. 6,468,203; 6,858,005 and U.S. patent application Ser. No. 10/988,212 filed 11112/2004, now U.S. Patent Application Publication US 2006/0052664, titled "Articulatable Connector Device for Endoscopes" each of which is incorporated herein by reference in entirety. The application and patents listed above are commonly assigned with this application.

The techniques described herein may be used to determine the shape of a bendable instrument by measuring or manipulating information related to the position of the control implements used to change the shape of or maneuver the instrument. The techniques described herein have several advantages. The techniques are independent of the force used for measurement as well as the tortuosity of the control elements used to maneuver the steerable instrument. The techniques repeatably and reliably reproduce the shape of the instrument. In addition, the techniques described herein enable the measurement and/or determination of steerable instrument shape using measurements of the control elements or cables used to control the instrument. Details of the various alternative embodiments for performing the methods of the invention will be appreciated after discussion of an exemplary bendable instrument and instrument control system.

Figure 1:
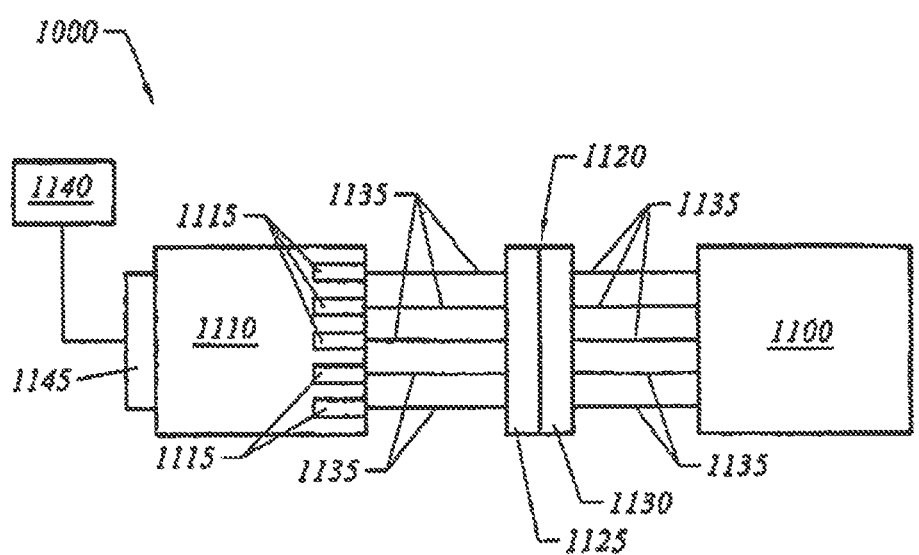
FIG. 1 shows a schematic view of a system for articulating a controllable article or bendable instrument.

FIG. 1 illustrates a schematic view of a system 1000 for moving a controllable article 1100, A force generator under control of one or both of a user input device 1140 and a system controller 1145 generates forces that are used to move the controllable article 1100. The forces generated by the force generator are transmitted to the controllable article using force connecting elements 1135 and a connector assembly 1120. The controllable article may also be an articulating instrument or a bendable instrument.

A connector assembly 1120 completes the transmission of power generated by the force generator i 110 and applied to the controllable article 1100. The two portions 1125, 1130 of the connector assembly 1120 are disengagably coupled. The connector portion 1125 is the first connector portion or the force generation side connector. The connector 1130 is the second connector portion or the controllable article side connector portion. When the connector portions 1125, 1130 are in a coupled condition, the force transmission elements 1135 are joined and force generated by the force generator 1110 is applied to the controllable article 1100. When the connector portions 1125, 1130 are not coupled, the connector portion 1130, force transmission elements. 1135 and the controllable article 1100 may be removed, in some embodiments as a single integrated unit, from the connector portion 1125, force transmission elements 1135 and the force generator 1110 or actuators 1115.

The connector assembly 1120 provides the ability to quickly connect and disconnect the two portions 1125, 1130 allows a single force transmission portion to be used with multiple controllable articles. Currently, articulating instruments such as, for example, endoscopes typically have only 4 cables to provide limited control at the tip of the endoscope. Moreover, the connector provides compact organization and efficient coupling of numerous force transmission elements used by highly maneuverable controllable articles. As described below, the connector may also house sensors.

As will be detailed below, the organization provided by the connectors could also provide other advantages to determining the bend of an instrument such as allowing efficient removal of cable slack or measurement of cable movement. Furthermore, the connector can be modified to allow attachment, placement, manipulation and/or operation of sensors used to measure the cables. The connector 1120 may include sensors and/or safety features to help ensure proper operation and articulation of the controllable article. In the discussion that follows, the connector refers to embodiments of the connector 1120 as well as embodiments of the first and second connector portions 1125, 1130. One sensor or feature may indicate or detect translation or movement of the engaging elements (i.e., carriage assemblies 120 described below) or the force transmission elements 1135 themselves. Another sensor or feature may also detect and measure or otherwise quantify the amount of translation or movement of the engaging elements (i.e., carriage assemblies 120 described below), the force transmission elements 1135 themselves or other indicia of the amount of control cable movement. Another sensor or indicator may be used to generate a signal based on contacting a known position used to correlate to the bend or position of the instrument.

Figure 2:
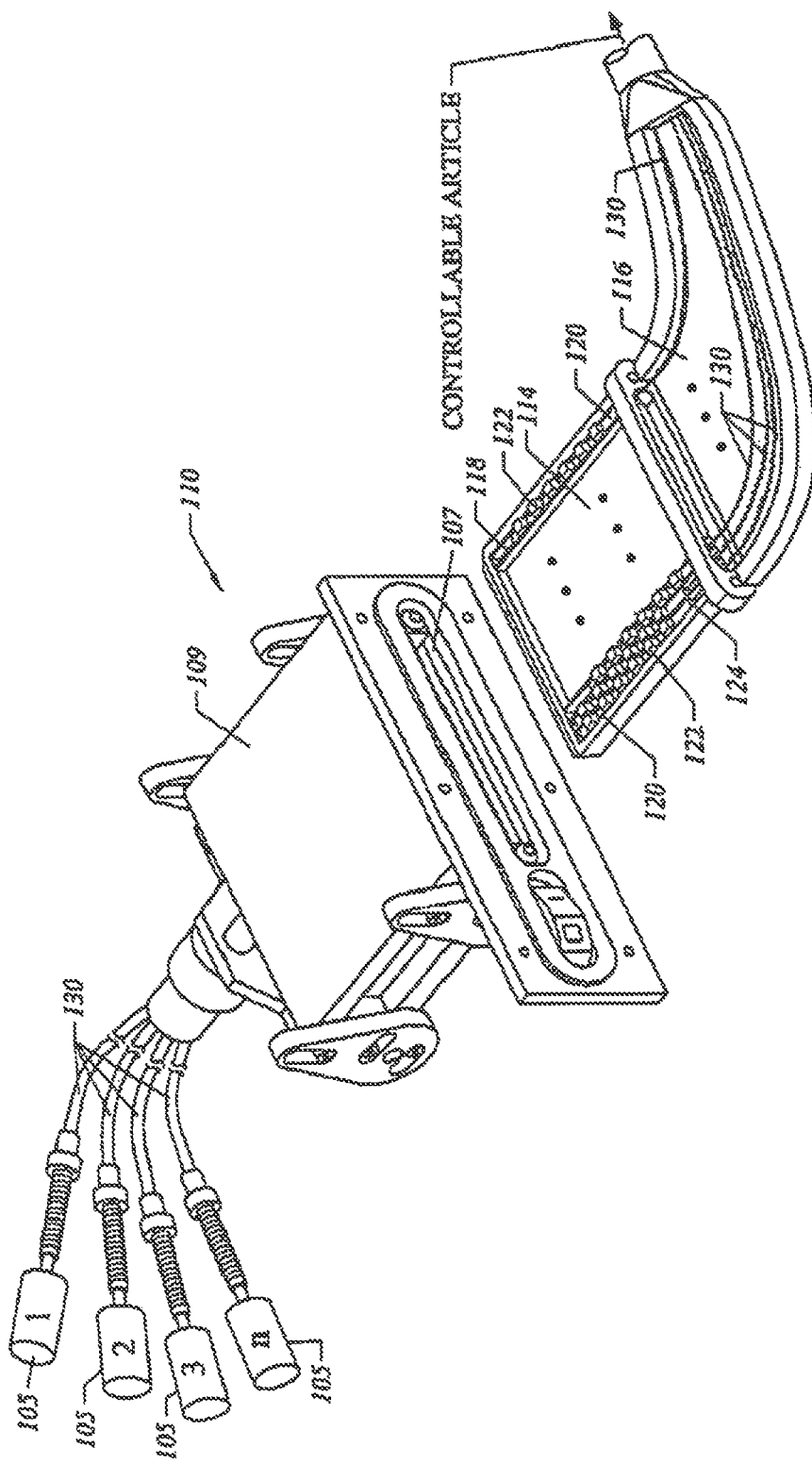
FIG. 2 is a perspective view of a connector assembly.

FIG. 2 illustrates a perspective view of a connector assembly 110 according to one embodiment of the present invention. The connector assembly 110 includes a first connector portion 112 (not shown but within housing 109) and a second connector portion 114. The first connector portion 112 is within the housing 109. The second connector assembly 114 includes a plurality of guide ways 118 each containing a carriage assembly 120. Each carriage assembly contains one or more than one engaging feature 122. Engaging features 122 on carriage assemblies 120, in the second connector portion 114 are adapted to engage with the engaging features 122 on carriage assemblies 120 of the first connector portion 112. One end of the carriage assemblies is connected to force transmission elements or cables 130. In the illustrated embodiment, the cables are Bowden cables. The cables run through a slack area 116. The slack area 116 allows added space for cable slack that may build up during controllable article movement. Thereafter, the cables are connected as desired to the controllable article.

The housing 109 provides a structural base for supporting the connector assembly 110. In this embodiment, the first connector portion 112 (not shown) is secured within the housing 109. The first connector portion and its carriage assemblies are connected via force transmission elements 130 to actuators 105. While four actuators 105 are illustrated, it is to be appreciated that more actuators may be used to drive a corresponding number of carriage assemblies. The housing 109 also provides an opening 107 configured to receive the second connector portion 114. Optionally, either one or both of the opening 107 or a portion of the second connector portion 114 may be keyed to ensure correct orientation prior to connection. When the second connector portion 114 is placed within the opening 107, the first and second connector portions 112, 114 are brought into engagement using an appropriate quick release mechanism, such as for example a cam actuated lever or other engagement device as known to those of ordinary skill in the art. When the first and second connector portion 112, 114 are engaged, forces generated by actuators 105 are transmitted to the controllable article.

Figure 3:
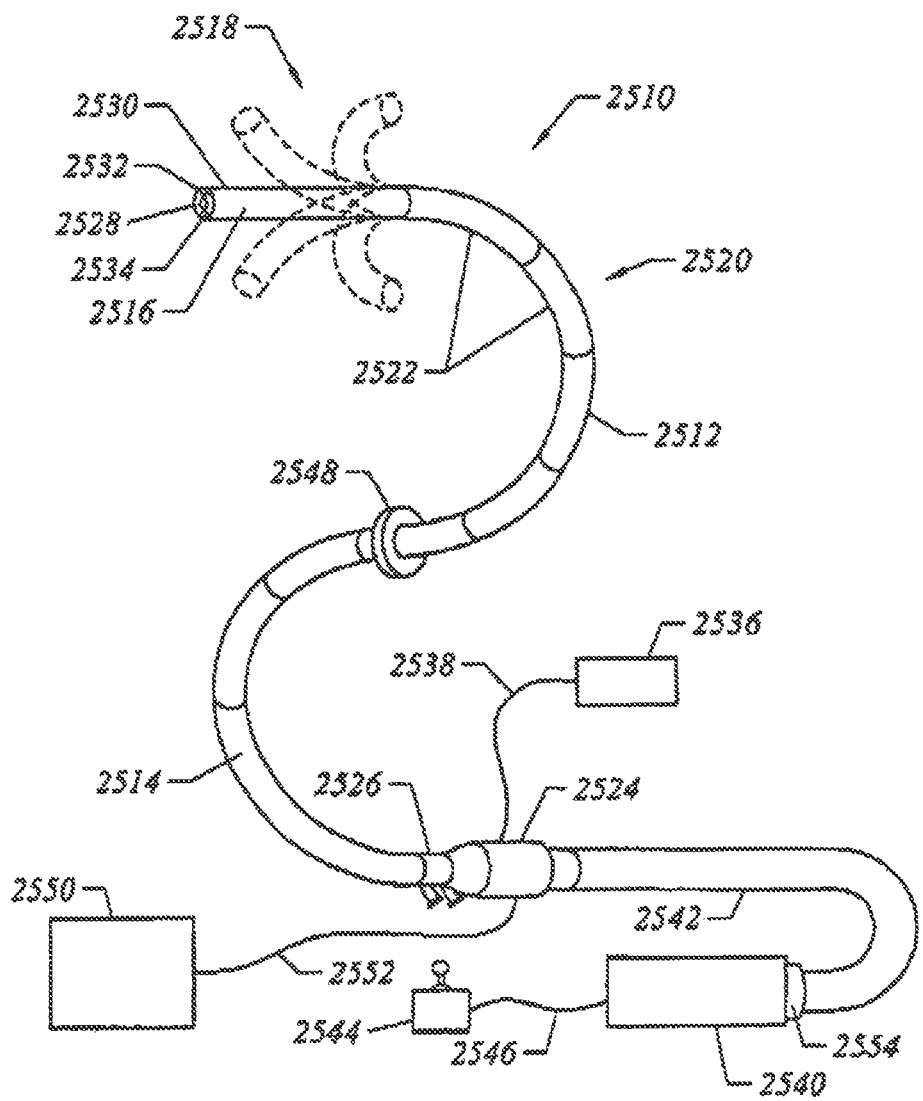
FIG. 3 illustrates an embodiment where the bendable instrument or controllable article is a segmented endoscope.

FIG. 3 shows an embodiment where the bendable instrument is a tendon driven endoscope 2510. The endoscope 2510 has an elongate body 2512 with a manually or selectively steerable distal portion 2516, an automatically controlled portion 2520, and a flexible and passively manipulated proximal portion 2514, which may be optionally omitted from the device. The steerable distal portion 2516 can be articulated by hand (i.e., using mechanical force of a conventional endoscope manual controls adapted to articulate segments) or with mechanical assistance from actuators. In addition, some embodiments allow a user to input steering commands (i.e., via a joystick 2544 or other input device) into a controller that translates the steering commands into endoscope segment movement.

The automatically controlled portion 2520 is segmented, and each segment is capable of bending through a full range of steerable motion. The distal portion 2516 is also a controllable segment. A more detailed description on the construction and operation of the segmented endoscope may be found in U.S. patent application Ser. No. 10/229,577 filed Aug. 27, 2002, which is incorporated herein by reference in its entirety.

The selectively steerable distal portion 2516 can be selectively steered or bent up to, e.g., a full 180 degree bend in any direction 2518, as shown. A fiber optic imaging bundle 2534 and one or more illumination fibers 2532 may extend through the body 2512 from the proximal portion 2514 to the distal portion 2516. Alternatively, the endoscope 2510 may be configured as a video endoscope with a miniaturized video camera, such as a CCO or CMOS camera, positioned at the distal portion 2516 of the endoscope body 2512. The images from the video camera can be transmitted to a video monitor by a transmission cable or by wireless transmission where images may be viewed in real-time and/or recorded by a recording device onto analog recording medium, e.g., magnetic tape, or digital recording medium, e.g., compact disc, digital tape, etc. LEDs or other light sources could also be used for illumination at the distal tip of the endoscope.

The body 2512 of the endoscope 2510 may also include one or more access lumens 2528 that may optionally be used for illumination, fibers for providing a light source, insufflation or irrigation, air and water channels, and vacuum channels. Generally, the body 2512 of the endoscope 2510 is highly flexible so that it is able to bend around small diameter curves without buckling or kinking while maintaining the various channels intact. When configured for use as a colonoscope, the body 2512 of the endoscope 2510 may range typically from 135 to 185 cm in length and about 13-19 mm in diameter. The endoscope 2510 can be made in a variety of other sizes and configurations for other medical and industrial applications.

Figure 9:
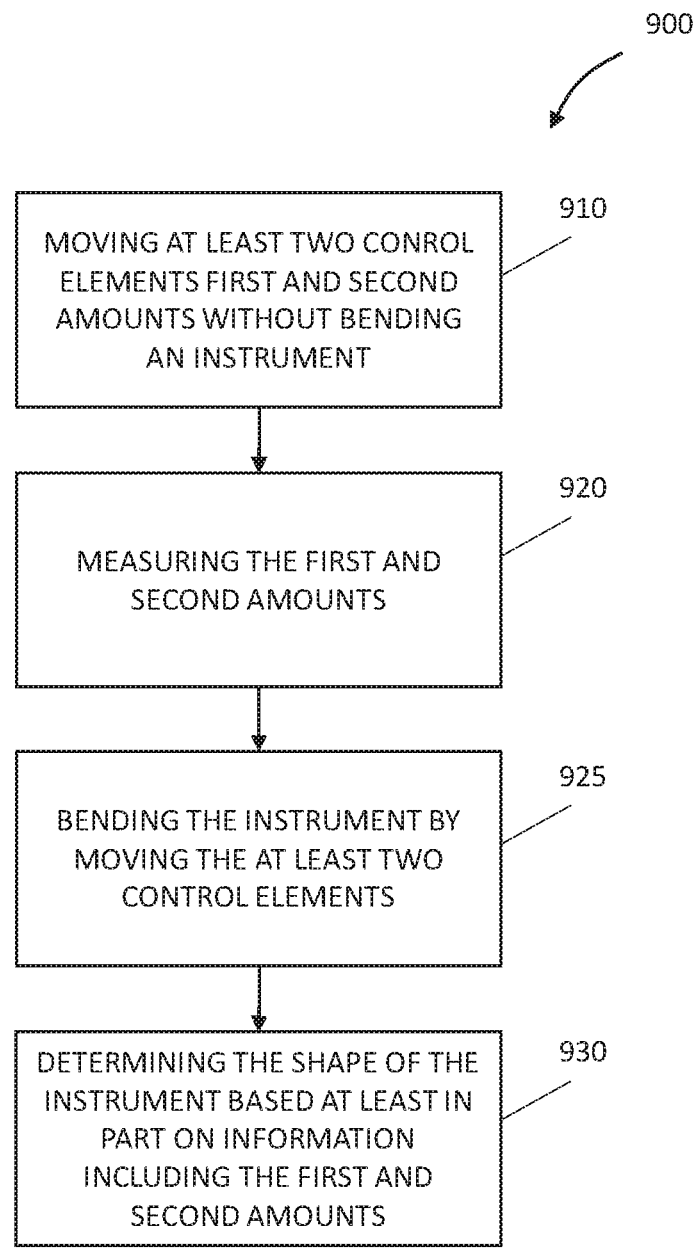
FIG. 9 is a flow chart illustrating a method of determining the position of an instrument.

The controllable portion 2520 is composed of at least one segment 2522, and preferably several segments 2522, which are, controllable via a computer and/or electronic controller 2540 located at a distance from the endoscope 2510. The segments 2522 may have forces transmission elements or tendons mechanically connected to force generators or actuators to allow for the controlled motion of the segments 2522 in space. The actuators driving the tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. The linear translation of the actuators within the controller may be configured to move over a relatively short distance to accomplish effective articulation depending upon the desired degree of segment movement and articulation. The movement of the actuators may be measured using sensors to provide input to the methods described below (FIG. 9).

Each segment 2522 preferably defines at least one lumen running throughout to provide an access channel through which wires, optical fibers, air and/or water channels, various endoscopic tools, or any variety of devices and wires may be routed. A polymeric covering, or sheath, 2530 may also extend over the body of the endoscope 2512 including the controllable portion 2520 and steerable distal portion 2516. This sheath 2530 can preferably provide a smooth transition between the controllable segments 2522, the steerable distal portion 2516, and the flexible tubing of proximal portion 2514.

A handle 2524 may be attached to the proximal end of the endoscope. The handle 2524 may include an ocular connected to the fiber optic imaging bundle 2534 for direct viewing. A cable 2552 provides a connection to a video monitor, camera, e.g., a CCD or CMOS camera, or a recording device 2550. An illumination source 2536 and an illumination cable 2538 is connected to or continuous with the illumination fibers 2534. Alternatively, some or all of these connections could be made at the controller 2540. Luer lock fittings 2526 may be located on the handle 2524 and connected to the various instrument channels.

The handle 2524 may be connected to a motion controller 2540 by way of a controller cable 2542. A steering controller 2544 may be connected to the motion controller 2540 by way of a second cable 2546 or it may optionally be connected directly to the handle 2524. Alternatively, the handle may have the steering control mechanism integrated directly into the handle, e.g., in the form of a joystick, conventional disk controllers such as dials, pulleys or wheels, etc. The steering controller 2544 allows the user to selectively steer or bend the selectively steerable distal portion 2516 of the body 2512 in the desired direction 2518. The steering controller 2544 may be a joystick controller as shown, or other steering control mechanism, e.g., dual dials or rotary knobs as in conventional endoscopes, track balls, touch pads, mouse, or sensory gloves. The motion controller 2540 controls the movement of the segmented automatically controlled proximal portion 2520 of the body 2512. This controller 2540 may be implemented using a motion control program running on a microcomputer or using an application specific motion controller.

The actuators applying force to the tendons may be included in the motion controller unit 2540, as shown, or may be located separately and connected by a control cable. The tendons controlling the steerable distal portion 2516 and the controllable segments 2522 extend down the length of the endoscope body 2512 and connect to the actuators. FIG. 3 shows a variation in which the tendons may pass through the handle 2524 and connect directly to the motion controller 2540 via a quick-release connector 2554. In this embodiment, quick release connector 2254 could be any of the above described connector or engagement assemblies. In this variation, the tendons may be part of the control cable 2542, although they could independently connect to the actuators, so long as the actuators are in communication with the controller 2540.

An axial motion transducer (also called a depth referencing device or datum) 2548 may be provided for measuring the axial motion, i.e., the depth change, of the endoscope body 2512 as it is advanced and withdrawn. The depth referencing device 2548 can be made in many possible configurations. For example, the axial motion-transducer 2548 in FIG. 3 is configured as a ring 2548 that may surround the body 2512 of the endoscope 2510. The axial motion transducer 2548 is preferably attached to a fixed point of reference, such as the surgical table or the insertion point for the endoscope 2510 on the patient's body. Depth referencing device 2S48, and different examples thereof; as well as segment articulation and cable operation are described in further detail in U.S. patent application Ser. No. 10/229,577 filed Aug. 27, 2002, which is incorporated herein by reference in its entirety.

Figure 4:
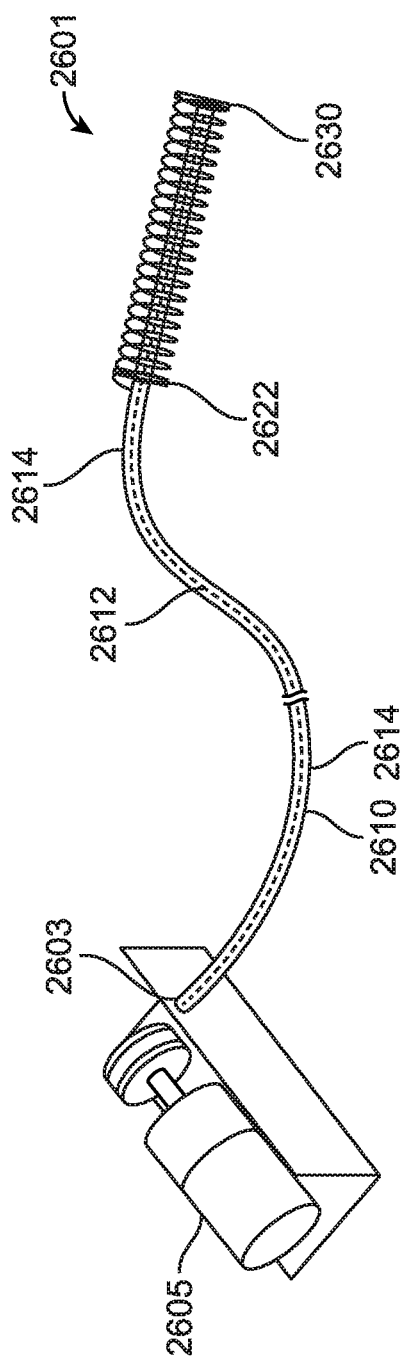
FIG. 4 shows a partial schematic representation of a single tendon bending a segment.

FIG. 4 shows a partial schematic representation of a single tendon bending a segment. For clarity, the other parts of a complete endoscope, including other tendons and segments, have been omitted from FIG. 4. Tension applied to a tendon cable is transferred across the entire segment, resulting in bending. The Bowden cable 2610 has a sleeve 2614 attached to the base 2622 of the segment 2601 and also fixed at the proximal actuator end 2603. The tendon cable 2612 is connected to the actuator 260S and the distal segment end 2630. By applying tension to the tendon 2612, only the intended segment 2601 is bent, and more proximal segments are unaffected. The tendon 2612 is placed in tension by the actuator 260S, which is show in this variation, as a motor pulling on the tendon cable 2612. Sensors may be provided on any of the components in FIG. 4 to provide information for the methods described below in FIG. 9.

Figure 5A:
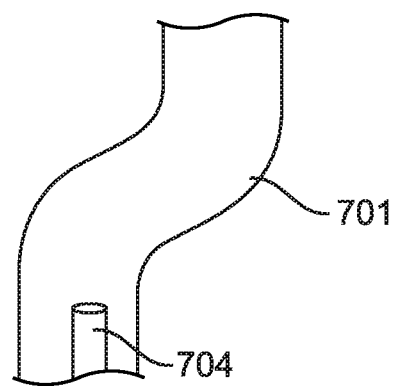
FIGS. 5A-5C illustrate an endoscope traversing a pathway.
Figure 5B:
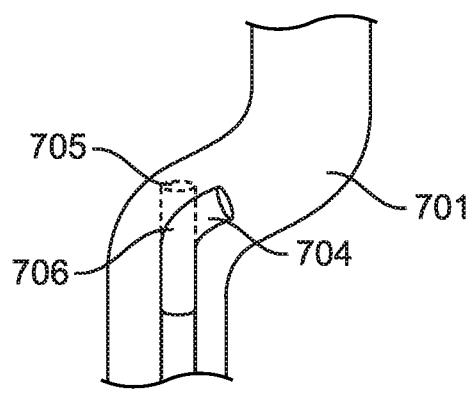
Figure 5C:
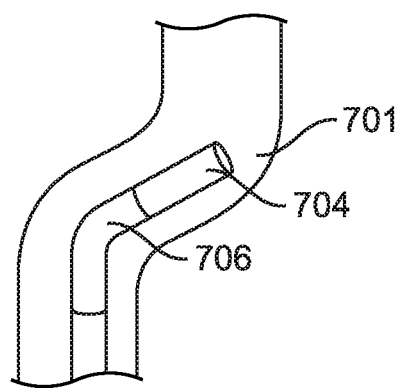

FIGS. 5A to 5C illustrate a variation of the tendon driven endoscope navigating a tortuous path. The path 701 is shown in FIG. 5A. This pathway may represent a portion of colon, for example. In FIG. 5A, the distal tip of the device 704 approaches the designated bend. FIG. 5B shows the distal tip being steered 705 (i.e., from the phantom position to the solid position) to assume the appropriate curve or bend 706. This steering could be performed manually by the user, e.g. a doctor, or automatically using an automatic detection method that could determine the proximity of the walls of the pathway or using images of the pathway generated by the instrument alone or in combination with images generated by an imaging modality outside of the instrument. As described, the bending of the steerable tip is performed by placing tension on the tendon, or combination of tendons that result in the appropriate bending.

The device is then advanced again in FIG. 5C. As it is advanced, the selected curve is propagated down the proximal length of the endoscope, so that the bend 706 of the endoscope remains in relatively the same position with respect to the pathway 701. This prevents excessive contact with the walls, and allows the endoscope to move more easily along the tortuous pathway 701. The endoscope is in continuous communication with the motion controller, and the motion controller can monitor the location of the endoscope within the pathway, e.g., depth of insertion, as well as the selected bends or curves that define the pathway of the endoscope. Depth can be determined by, e.g., the axial motion transducer 2548 previously described, or by more direct measurement techniques. Likewise, the shape of each segment could be determined by the tension applied to the tendons, or by direct measurement, such as direct measurement of displacement of the tendon cables. The motion controller can propagate the selected shape of a segment at a specified location, or depth, within the body, e.g., by setting the lengths of the sides of more proximal segments equal to the corresponding lengths of the sides of more distal segments as the device is moved distally. The controller can also use this information to automatically steer the body of the endoscope, or for other purposes, e.g. creating a virtual map of the endoscope pathway for analytic use.

In addition to measuring tendon displacement, the motion controller alone, a connector of the present invention alone or the controller and the connector operating together can also adjust for tendon stretch or compression. For example, the motion controller can control the "slack" in the tendons, particularly in tendons that are not actively under tension or compression. This action by the motion controller may be used in the methods of the invention as described below. Allowing slack in inactive tendons reduces the amount of force that is required to articulate more proximal segments. In variations described above the umbilicus at the distal end of the endoscope may contain space to allow slack in individual tendons.

The bending and advancing process can be done in a stepwise or continuous manner. If stepwise e.g., as the tendon is advanced by a segment length, the next proximal segment 706 is bent to the same shape as the previous segment or distal steerable portion. A more continuous process could also result by bending the segment incrementally as the tendon is advanced. This could be accomplished by the computer control; for example when the segments are smaller than the navigated curve.

Figure 6:
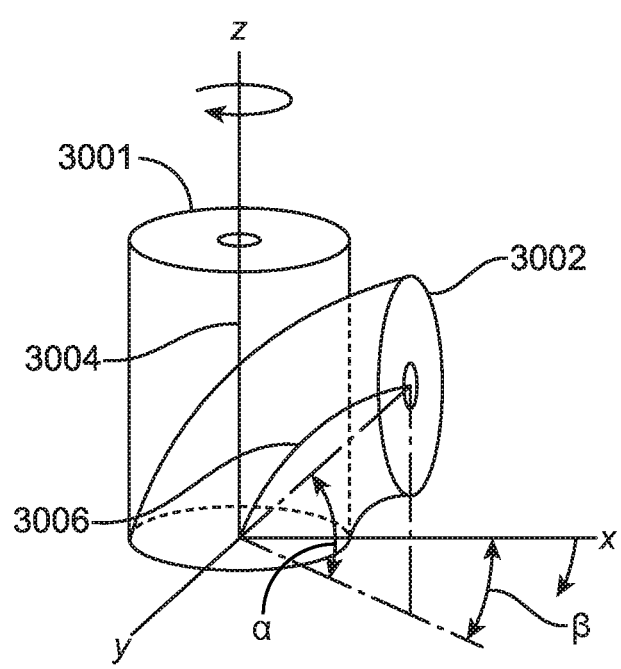
FIG. 6 describes the range of motion of bending through the use of three control cables.

FIG. 6 shows an example of the resulting segment articulation which may be possible through the use of two or three tendons to articulate the controllable segments, including the steerable distal section. FIG. 6 shows one example of a possible range of motion of a controllable segment of the present invention actuated, in this example, by three tendons. A segment in the relaxed, upright position 3001 can be bent in virtually any direction relative to the x-y plane. The figure, as an illustrative example, shows a segment 3002 that has been bent down and at an angle relative to its original position 3001. The angles alpha ($\alpha$) and beta ($\beta$) describe the bend assumed by the segment. Angle beta describes the angle in the x-y plane and angle alpha describes the angle in the x-z plane. In one variation, the controllable segments of the endoscope can bend through all 360 degrees in the angle and up to 90 degrees in the a angle. An angle $\alpha$ greater than 90 degrees would result in looping of the endoscope. In FIG. 6, the segment is shown bent approximately 45 degrees along angle $\alpha$. The freedom of movement of a segment is, in part determined by the articulation method, the size of the segment, the materials from which it is constructed, and the manner in which it is constructed, among others. Some of these factors are discussed herein.

The steerable distal portion, as well as the endoscope and the controllable segments are bendable but preferably not compressible or expansible. Thus, in FIG. 6, the centerline 3004 of the relaxed segment 3001 is approximately the same length as the centerline 3006 of the segment after bending 3002.

Figure 7A:
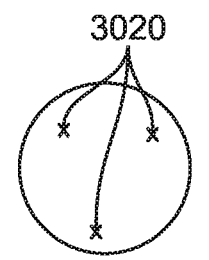
FIGS. 7A-7E show the use of three control elements to bend a segment.

FIGS. 7A to 7E show the use of three tendons to actuate a segment in a bendable instrument. The control elements shown in this example are all Bowden type cables 3010 that have an internal cable 3012 coaxially surrounded by a housing or sleeve 3014 in which the cable is free to move. Bowden cables can be used to apply either tensile or compressive forces, i.e., they may be pushed or pulled, to articulate the endoscope and can be actuated remotely to deliver forces as desired at locations along the endoscope. Force from a tendon is exerted across or through the segment by attaching the tendon cable at the distal end of the segment 3020 and the tendon housing 3014 at the proximal end of the segment 3022. FIG. 7A shows a view of the top of the segment with three attachment sites for the tendon cables indicated 3020.

In one variation, three tendons are used to actuate each segment, including the steerable distal portion, although four or more tendons could be used. Three tendons can reliably articulate a segment in any direction without having to rotate the segment or endoscope about its longitudinal axis. The three cable tendons 3012 are preferably attached at the distal end of the segment 3020 close to the segment's edge, spaced equally apart. In FIG. 7A, tendons are attached at the two o'clock, six o'clock and 10 o'clock positions. It is desirable to use fewer tendons, because of space concerns, since the tendons controlling each segment project proximally to the actuators. Thus, two tendons could be used to control a segment it may also be desirable to include one or more biasing element, e.g., a spring, to assist in articulating a segment in three dimensions. In another variation, two tendons may be used to bend a segment in three dimensional space by controlling motion in two directions while rotating the segment about its longitudinal axis.

Figure 7B:
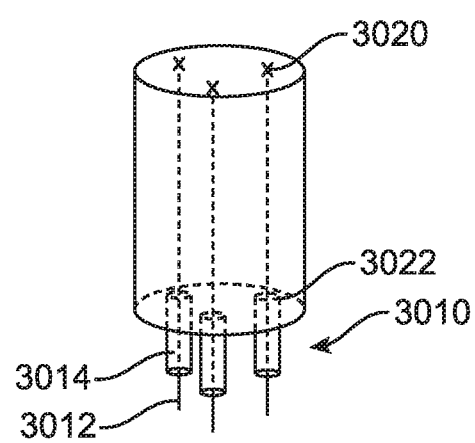
Figure 7C:
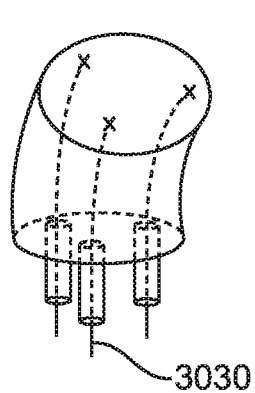
Figure 7D:
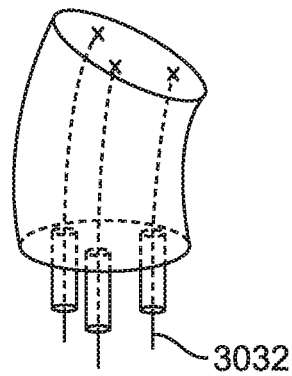
Figure 7E:
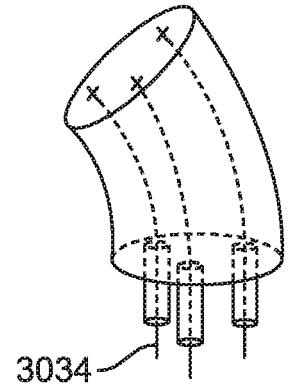

FIG. 7B shows a relaxed segment with three tendons attached. The tendon sleeves 3014 are shown attached to the proximal end of the segment 3022 directly below the corresponding cable attachment sites. FIGS. 7C, 7D and 7E show this segment bent by each of the controlling tendons 3010 separately.

As shown in FIG. 7C, applying tension by pulling on the first tendon 3030 results in a bending in the direction of the first tendon 3030. That is, looking down on the top of the unbent segment (as in FIG. 7B), if the first tendon is attached at the six o'clock position, then pulling on just this tendon results in bending the segment towards the six o'clock position. Likewise, in FIG. 7D, putting tension only on a second tendon 3032 attached at the two o'clock position results in bending the segment towards the two o'clock direction. Finally, pulling on the tendon in the ten o'clock position 3034 bends the segment towards the ten o'clock direction. In all cases, the bending is continuous; the greater the tension applied, the further the bending (the a angle, in the x-z plane of FIG. 6). A segment can be bent in any direction by pulling on individual tendons or a combination of two tendons. Thus, to bend the segment in the twelve o'clock direction, both the second 3032 and the third 3034 tendon could be pulled with equal force. Alternatively, first tendon 3030 in the six o'clock position may be pushed either alone or in combination with second 3032 and third tendons 3034 being pulled to result in the same configuration.

In all these variations, the circumferential locations of the tendons and/or biasing elements are illustrative and are not intended to be limited to the examples described herein. Rather, they may be varied according to the desired effects as understood by one of skill in the art.

Figure 8A:
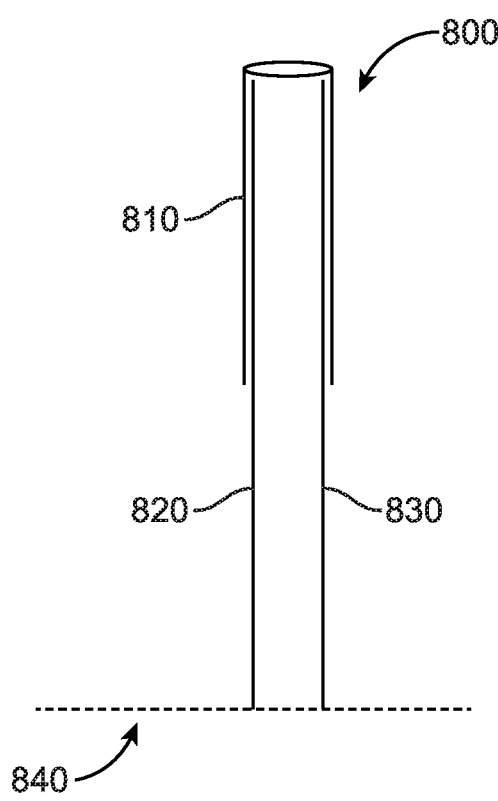
FIGS. 8A and 8B illustrate the use of two control elements to bend a segment.
Figure 8B:
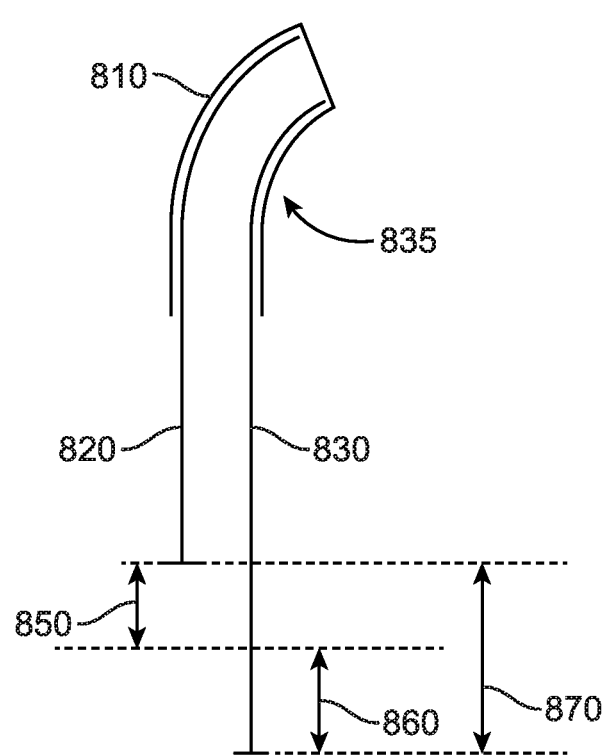

FIGS. 8A and 8B illustrate a simplified segment 810 of a bendable instrument 800. Segment 810 is one segment within the bendable instrument that may be configured as described above in FIGS. 1 and 3, for example. Control elements 820, 830 are similar to those described above and are actuated to bend the segment 810. Two control elements are illustrated for simplicity of explaining the methods of the invention. The invention is not however limited only to bending segments using only two control elements or to segments having only two control elements. Three control elements (i.e. ", FIGS. 6 and 7) or more control elements could be used to provide the desired degree of control. The techniques of embodiments of the invention may also be applied, for example, to a steerable instrument and control system that utilizes articulating segments with two opposing control elements, such as wires, for each axis of articulation. Alternatively, in a three element system, an articulating segment with three control elements acting in concert to control both axes of articulation.

Complementary control elements operate cooperatively to control the bend of a segment. Two or a pair of complementary control elements may be used to control the bend of an instrument within a plane, for example. As illustrated in FIGS. 8A, 8B, control elements 820, 830 are a complementary pair of control elements for the segment 810. The plane of articulation is within the page. In FIG. 8A the control elements 820, 830 are shown in the neutral position 840 where the segment 810 is straight or non-bent. In normal use, articulation of the exemplary segment 810 is achieved by pulling one control element while leaving the opposing control element slack. FIG. 8B shows the segment 810 bending to the right into position 835. The position 835 is achieved when the segment 810 bends by pulling on control element 830 while control element 820 is slack. As a result, pulling control element 830 moves the control element 830 an amount 860 from the neutral position 840. The movement of the segment 810 into position 835 moves control element 820 an amount 850 from the neutral position 840.

The flow chart 900 in FIG. 9 illustrates an embodiment of a method of determining the shape a bendable instrument according to the invention. The first step, step 910, includes moving at least two control elements first and second amounts without bending the instrument. In one embodiment, the step of positioning the bendable instrument within a lumen is performed before the moving step.

The second step, step 920, includes measuring the first and second amounts. At 925, the method includes bending the instrument by moving the at least two control elements, as further discussed in connection with FIGS. 8A and 8B.

The position or amount of movement of the control elements can be measured using any suitable indication or device in any suitable position. The amount of control element movement may be obtained through measurement or indication taken on the control side such as system controller 1145, an actuator connected to a control element, or the force generator 1110 via encoder or other suitable measurement device. The amount of control element movement may be obtained through measurement or indication taken on any of the components illustrated in FIG. 4. The amount of control element movement may be obtained through measurement or indication taken from a sensor on or in a connector that joins the bendable instrument to an actuator. Exemplary connectors include embodiments of the articulatable connector 110 illustrated in FIG. 2 and further described in U.S. patent application Ser. No. 10/988,212 now U.S. Patent Application Publication US 2006/0052664 titled "Connector Device For A Controllable Instrument." The amount of control element movement may be obtained through measurement or indication taken on a bendable instrument, the controllable article 1100 illustrated in FIG. 1, the segmented instrument 2510 in FIG. 3, the segment 2601 or the cable 2612 in FIG. 4.

Any of the components of the controllable instrument, the connector (if present) or the control or actuation system may be modified to include sensors. These sensors are adapted based on their position in the system and relationship the control cables to provide measurement of the amount of control cable movement or other information useful for embodiments of the invention. Sensors may be located in either or both of the connector portions 112, 114 or in any of the connection and release mechanisms described herein. Any of a wide variety of commonly available sensors may be used to accomplish the functionalities described herein such as, for example, reed switches, electro-optical switches, resistive switches, contact switches, optical indicators, strain gauges, stress gauges, measurement indicators and the like. Sensors may be used to provide a tension measurement taken in a connector that couples an actuator to one of the at least two control elements. In one embodiment, the measurement instrument is an optical encoder. In one embodiment, the tensioning element or actuator is a permanent magnet brushed DC motor. Movement of the DC motor may be measured, controlled and monitored using an optical encoder.

A sensor or sensors may provide input to a feedback loop used to monitor performance of the steps in method 900. A sensor may be used to monitor slack removal from control elements. In one aspect, the input from the sensor is related to a tension measurement of a control element.

Additionally, the output or signal from a sensor may be integrated into the control system. For example, sensors within the connector could be used to measure carriage assembly movement inside of a connector as the indication for measuring amounts of control cable movement. Such a sensor may be coupled to or in communication with a portion of the connector assembly and have an output that indicates the control cable position. Furthermore, the control system could be adapted to use the output of the sensor, in place of or in addition to encoders on the instrument to control and/or monitor the position, shape, and movement of the instrument. It is to be appreciated that sensors used herein may be adapted to provide information used during the moving step 910, the measuring step 920 and/or the determining step 930.

In a specific example where the controllable article is a steerable endoscope, the tip of the endoscope and different segments or positions of the endoscope could be determined using the position of the carriage assembly/assemblies and cables used to control those segments. In another example, a sensor may be used to determine the length of travel of a carriage assembly. The length of travel of a carriage assembly may be used to correspond to or be part of the measuring or determining step of the present invention. For example, predetermined relationships between the carriage assembly position and the segment angle (i.e., using look up tables or kinematics relationships) could be used as part of the determining step.

Embodiments of the connector described in FIG. 1 may be particularly well suited for determination of position of the control cables using the position and/or movement of the cables or carriage assemblies or other components within the connector 1120. For example, the position, shape, and/or movement of the tip of a steerable endoscope or portion thereof could be measured and/or determined using the position of the cables, carriage assemblies or other components within the connector 1120. The amount of within connector movement of the cables, carriage assemblies or components may be correlated to an amount, degree or type of bending or instrument position. As such, by monitoring, measuring and/or determining within connector movements, the position of the tip, sections, segments or modules of a controllable article may be determined using the methods of the invention. In some embodiments, measurement of linear motion of a control cable within the connector may be used to determine segment position including the position and movement of the instrument tip. Sensors to detect movement may be placed in one or both connector portions 112, 114 or elsewhere on the instrument, an actuator using to articulate the instrument or in the control system.

Optionally, the slack may be removed from the control elements before the instrument bending, measuring, or determining steps. In one embodiment, the step of removing slack from the control elements is performed before the measuring step. In one example, accuracy of control element measurement is achieved by simultaneously pulling all control elements with a constant force to remove the slack from the control elements. Simultaneously pulling all of the control elements reduces the likelihood that the removal of the slack would change the position of the instrument and adversely impact the measurement technique.

One embodiment of the method includes the step of removing slack from the at least two control elements of the set of control elements before the measuring step. While the removal of slack can lead to increased accuracy, inadvertent instrument segment movement during slack removal will diminish accuracy. As such, the removing step is completed without changing the position of the instrument. One way to ensure that the position of the instrument is not changed is to power an actuator with a known drive command. In one alternative, a drive command is selected that is insufficient to change the position of the instrument. One type of drive command is the drive current used to operate an actuator. A low drive current may be selected and used to remove slack but not result in articulation. While the low drive current ensures that segment movement does not occur, it may remove slack at a slow rate. In an alternative slack removal technique, there is provided the step of removing the slack from the at least two control elements during a first time period at a first force limit before removing the slack from the at least two control elements during a second time period at a second different force limit. In one alternative, the first force limit is less than the second force limit. The use of a two step slack removal process allows a lower force to be applied first for a short period of time for gross slack removal. Then, after the first time period has elapsed and when it is likely that the gross slack is removed, the force limit for slack removal is increased. In any event, the force limits selected are insufficient to result in segment articulation. This method could be used on the non-controlling wire of a wire set. For example, pull the slack out of the wire not currently being used for control to gain a measurement of the angle or position actually achieved. It is to be appreciated that the concept of removing slack, generally understood in the context of flexible control elements, may also be applied to control rods, semi-rigid control elements or rigid control elements by placing the control element under tension to improve the reliability and repeatability of the steps of the inventive method.

In one alternative of the two step force removal technique, the first step is a high speed removal at a low force. Next, the speed of removal is reduced and the force of removal increased. In this way the first step quickly removes the gross slack and the second step confirms the removal of slack and holds the wires in tension for increased accuracy during the measuring step. In the case where complementary control cables are used, the counter balancing action of the wires mitigates any tendency of the applied slack removal forces to result in segment articulation.

The third step, step 930, includes determining the shape of the instrument based at least in part on information including the first and second amounts.

After moving the control elements to bend a segment and then measure the amount of movements, the next step is to determine the position of the instrument from the measured amounts. One technique to aid in the removal of common mode factors involves the use of a position delta. The technique is independent of the force used for measurement as well as the tortuosity of the control elements used to maneuver the steerable instrument. The position delta is used to normalize the obtained measurement information for a control cable. The position delta may be explained through reference to FIGS. 8A and 8B. The position delta can be calculated by subtracting a neutral or calibrated position from a measured position. The position delta for controllable element 820 is obtained by subtracting the neutral position 840 from the measured position 850. Similarly, the position delta for controllable element 830 is obtained by subtracting the neutral position 840 from the measured position 860. In one aspect, the determining step uses a calculated position delta of the at least two control elements. In one embodiment, summing the position deltas 870 from opposing control elements such as control elements 820, 830 yields a result which has a relationship with the bend, angle or shape of the segment.

In one embodiment, the determining step uses a calculated position delta of complementary control elements within the at least two control elements. In an alternative embodiment, the determining step uses a calculated position delta of a pair of opposing control elements within the at least two control elements. The relationship between the opposing control elements position delta or sum of the position deltas and the shape or angle of the segment is essentially independent of the tortuosity/friction in the cables and of the force used in the measurement. In one embodiment, summing the position deltas from opposing control elements yields a result which has a linear relationship with the angle of the segment. Numerous techniques may be used to perform the determining step. In one technique, the determining step comprises using a look up table that correlates the first and second amounts to the instrument position. In yet another technique, the determining step comprises using a modeled kinematic relationship between first and second amounts and the instrument positions.

In one embodiment of the method of the invention, complimentary control elements are used to measure the angle a segment has taken after the control elements have been relaxed. When the control elements are relaxed, the instrument is allowed to assume the shape of its surroundings. The surroundings act as an external force to move the instrument. Information determined using the methods of the invention such as the bend, position, shape, or angle of the instrument at this time may be used as an indication of the shape of the surroundings influencing the position, shape or angle of the instrument. This is one way of using the determining step to determine the shape of the lumen. As a result, the moving step is accomplished without using an actuator connected to a control element. In another embodiment, the moving step is performed by the lumen acting on the instrument.

In an alternative embodiment of the measuring step, the position of the instrument is determined using a control element not being used to control a segment (i.e., a slack cable). In this alternative, the measuring step includes moving a control element not being used to bend the instrument. Thereafter, perform the step of determining a calculated position delta for the control element not being used to bend the instrument. The position delta can then be used as described above. In another aspect of this alternative, the determining step uses the calculated position delta for a control element not being used to bend the instrument. As such, moving may be accomplished by forces external to the instrument.

It is to be appreciated that the moving, measuring and determining techniques described herein may also be used to determine the neutral position 840. The ability to accurately control an instrument. is based in part on the ability to repeatably and reliably determine a neutral or calibration position. One exemplary position is the straight or unarticulated position illustrated in FIG. 8A. The instrument may be held manually or secured to a calibration fixture that holds the instrument in the desired calibration position. Once in the desired position, the slack is removed from all of the control elements to measure and determine the neutral or calibration position 840 for each control element. The techniques described herein may be used periodically to determine and/or confirm the characteristics of the control cables relative to the neutral or calibration condition. In this way, changes in control element performance due, for example, to temporary elongation (i.e., stretch) or permanent elongation (i.e., cable construction or creep) may be monitored and used to compensate for control element changes.

Although the endoscope connectors and assemblies have been described for use with colonoscopes, the connector and engagement assemblies of the present invention may be configured for the efficient control of a wide variety of controllable articles in the a number of other medical and industrial applications. In addition, they can also be configured for use with catheters, cannulas, surgical instruments, interluminal instruments, and/or introducer sheaths that use the principles described above for navigating through body channels or within the body. They may also be used for industrial applications such as inspection and exploratory applications within tortuous regions, e.g., machinery, pipes, difficult to access enclosures and the like.

In yet another variation, the motion controller assemblies can be used to control the automatically controlled proximal portion to follow the selected path and, if necessary, to return to a desired location using the three-dimensional model in the electronic memory of the controller. While the above illustrative embodiments have described mechanical connections and force transmissions of the first and second connector portions, it is to be appreciated that alternative embodiments of the connector of the present invention may be modified and adapted to accommodate other forms of energy, position, or force transfer including but not limited to, electrical, pneumatic, hydraulic and the like. Modification of the above described assemblies and methods for carrying out the invention, and variations of aspects of the invention that are obvious to those of skill in the art are intended to be within the scope of the claims.

What is claimed is:

1. A method for determining a shape of a bendable instrument, comprising:
 placing the bendable instrument in a neutral position;
 while the bendable instrument is in the neutral position, moving a first control element a first amount until slack is removed from the first control element;
 while the bendable instrument is in the neutral position, moving a second control element a second amount until slack is removed from the second control element;
 sensing a position of the first control element after moving the first control element the first amount, the sensed position of the first control element being defined as a first control element calibration position;
 sensing a position of the second control element after moving the second control element the second amount, the sensed position of the second control element being defined as a second control element calibration position;
 bending the instrument from the neutral position by moving one or both of the first control element and the second control element from the respective first control element calibration position and the second control element calibration position;
 measuring a first movement amount the first control element moved from the first control element calibration position to determine a first measured position;

measuring a second movement amount the second control element moved from the second control element calibration position to determine a second measured position; and determining a resulting shape of the bendable instrument by correlating the first movement amount and the second movement amount with the shape of the bendable instrument based on a modeled kinematic relationship or based on correlation values stored in a look up table.

2. The method of claim 1, wherein moving one or both of the first control element and the second control element from the respective first control element calibration position and second control element calibration position comprises moving one or both of the first control element and the second control element by applying an external force to the bendable instrument.

3. The method of claim 2, wherein applying an external force to the bendable instrument comprises moving the instrument against a patient's body.

4. The method of claim 1, wherein moving one or both of the first control element and the second control element from the respective first control element calibration position and second control element calibration position comprises moving one or both of the first control element and the second control element using an actuator operably coupled to the bendable instrument.

5. The method of claim 1, wherein moving the first control element the first amount until slack is removed from the first control element and moving the second control element the second amount until slack is removed from the second control element comprises tensioning the first control element and the second control element using one or more actuators operably coupled to the first control element and the second control element.

6. The method of claim 5, wherein moving a first control element a first amount until slack is removed from the first control element and moving a second control element a second amount until slack is removed from the second control element comprises sending a predetermined drive command to the one or more actuators.

7. The method of claim 6, wherein the predetermined drive command causes the one or more actuators to apply a force to the first control element and to the second control element, the force being insufficient to move the bendable instrument front the neutral position.

8. The method of claim 1, wherein positioning the bendable instrument in the neutral position comprises positioning the bendable instrument in a straight configuration.

9. The method of claim 1, wherein sensing the position of the first control element comprises sensing the position of the first control element with a first sensor operably coupled with a controller, and sensing the position of the second control element comprises sensing the position of the second control element with a second sensor operably coupled with the controller.

\* \* \* \* \*